United States Patent [19]
Layzell et al.

[11] Patent Number: 5,096,294
[45] Date of Patent: Mar. 17, 1992

[54] METHOD AND APPARATUS FOR MEASURING OXYGEN CONCENTRATION AND ITS SUBSEQUENT USE IN ESTIMATING NITROGEN FIXATION IN PLANTS

[75] Inventors: David B. Layzell; Stephen Hunt, both of Kingston; Gerry Palmer, Sydenham, all of Canada; R. Ford Denison, Beaver, W. Va.

[73] Assignees: Queen's University at Kingston, Ontario, Canada; The United States of America as represented by the Department of Agriculture, Washington, D.C.

[21] Appl. No.: 671,239

[22] Filed: Mar. 19, 1991

Related U.S. Application Data

[63] Continuation-in-part of Ser. No. 495,732, Mar. 19, 1990, abandoned.

[51] Int. Cl.$^5$ .............................................. G01N 21/27
[52] U.S. Cl. .................................... 356/326; 356/328; 356/407; 356/419
[58] Field of Search ................. 356/41, 300, 326, 328, 356/402, 407, 416, 418, 419, 432–435, 446–448

[56] References Cited

U.S. PATENT DOCUMENTS 4,938,699  7/1990  Cassagne .................. 73/432.1

*Primary Examiner*—F. L. Evans
*Attorney, Agent, or Firm*—Richard J. Hicks

[57] ABSTRACT

A non-invasive method and apparatus are described for measuring the oxygen concentration in the infected cells of the nodules of nitrogen fixing plants in the laboratory or field. In many cases, this information can be used to estimate the nitrogenase activity, and therefore the nitrogen fixation rate, in these nodules since recent studies have shown that the oxygen concentration limits and controls nitrogenase activity under most environmental conditions. Using the same apparatus, a method to measure nodule respiration and nodule oxygen permeability is also described. The nodule oxygen concentration in the infected cells of nodules is maintained at very low levels and has not been measurable previously by non-invasive techniques. The fractional oxygenation of plant hemoglobin is measured spectroscopically using one or more modulated light sources, a number of optical fibres to convey the light to and from the nodules, a photodetector to measure the light passing through the nodule and a detection system such as a photodiode coupled to a microcomputer or a lock-in amplifier to process the output signal.

43 Claims, 7 Drawing Sheets

METHOD AND APPARATUS FOR MEASURING OXYGEN CONCENTRATION AND ITS SUBSEQUENT USE IN ESTIMATING NITROGEN FIXATION IN PLANTS

CROSS REFERENCE TO RELATED APPLICATION

This application is a continuation-in-part of prior application Ser. No. 495,732 filed 19 Mar. 1990, in the names of David B. Layzell, Stephen Hunt and Gerald R. Palmer and now abandoned.

FIELD OF INVENTION

This invention relates generally to a method and apparatus for (a) measuring the oxygen concentration in nodules and (b) using this information to estimate nitrogenase activity and nitrogen fixation rate in these plant organs. More particularly, this invention relates to an apparatus for measuring the fractional oxygenation of plant hemoglobin and thereby the oxygen concentration in root nodules in $N_2$ fixing plants. Studies show that under many conditions, this concentration regulates nitrogenase activity and can be used to estimate the rate of nitrogen fixation in nodules. A method is also described for using the apparatus to measure the rate of $O_2$ consumption by the nodule as well as the permeability of the nodule to $O_2$ diffusion. These factors are important in nodule metabolism and are frequently correlated with nitrogenase activity.

BACKGROUND OF INVENTION AND PRIOR ART

Nitrogen is an essential element for plant growth. A number of plants such as the legumes (soybean, peas, beans, alfalfa, clover, peanut, black locust, etc.) and various woody angiosperms (alder, casuarina, etc.) are able to provide their nitrogen requirements by forming a symbiotic association with certain soil bacteria. The bacteria live within root (or in some species, stem) structures called nodules where they reduce atmospheric nitrogen gas ($N_2$) to a form of nitrogen that the plant can use in the production of protein, DNA, etc. Therefore, these plants do not require expensive and environmentally harmful nitrogenous fertilizers to support their growth and provide commercially acceptable yields. Nitrogenase is the bacterial enzyme responsible for nitrogen fixation. However, not all of nitrogenase activity is associated with $N_2$ fixation, since a portion (usually 25-40%) of the activity involves hydrogen gas production.

Biological nitrogen fixation will play an increasingly important role in future agricultural practice. However, the process is very sensitive to several environmental factors such as drought stress or the presence of nitrogenous fertilizer in the soil. In these situations, studies with legumes have shown that the nodule restricts oxygen diffusion to the bacteria and consequently nitrogenase activity declines due to severe oxygen limitation. In a field situation, it is very difficult to determine whether the nodules are actively fixing nitrogen gas and therefore difficult to know whether or not to take remedial action. Since most legume nodules are very sensitive to disturbance, it is not possible to dig up the root system in order to determine nodule activity by any of the known methods. Known methods for measuring symbiotic nitrogen fixation include:

(a) The plant nitrogen increment method in which plants are harvested at different times and their nitrogen content is measured. This method is time consuming, destructive and does not distinguish between $N_2$ fixation and fertilizer nitrogen uptake. It also requires an expensive chemical assay, and when the result is known it is generally too late to take any required action to increase nitrogen input into the crop.

(b) Isotopic methods in which the $^{15}N$ and $^{14}N$ content of plant tissues are measured. Due to differences between combined nitrogen ($NO_3^-$, $NH_4^+$) assimilation and $N_2$ fixation in the assimilation of $^{15}N$ and $^{14}N$-containing molecules, it is possible to estimate rates of $N_2$ fixation from a knowledge of the isotopic composition of the plant, soil and atmospheric N pools. Alternatively, enriched levels of $^{15}NO_3^-$ or $^{15}N_2$ can be provided to the plant and the contribution of each N source can be measured over a defined interval of time. These isotopic methods are destructive, time consuming, require expensive isotopes and analytical instrumentation and by the time the result is obtained, it would likely be too late to take remedial action for the crop.

(c) The acetylene reduction assay method in which the plant roots and nodules are exposed to 10% acetylene, and the production of ethylene is measured over time. The $N_2$ fixing enzyme, nitrogenase, uses acetylene as an alternative substrate and reduces it to ethylene. While the method is quick, relatively inexpensive and, in theory, measures nitrogenase activity directly, it is notorious for producing artifactual results. Also expensive equipment is needed and it is usually destructive to the plant.

(d) Monitoring hydrogen gas production, a by-product of nitrogenase activity, from nodulated roots in air and $Ar:O_2$ gas. While the method is non-invasive and relatively inexpensive, not all symbiosis evolve the hydrogen gas that is produced by the nitrogenase enzyme. Also, the method would be difficult to use in field studies.

It will be apparent that none of the above techniques are of much use to Plant Breeders who want to screen large numbers of plants for maximal nitrogenase activity under normal field conditions. Neither are they of use to farmers who need to know whether their $N_2$-fixing crops are actively fixing the nitrogen they will need for optimal growth and yield, and therefore whether or not they should irrigate and/or apply chemical fertilizer. What is needed, therefore, is a rapid, non-invasive technique to obtain a reasonably accurate estimate of nitrogen fixation in plants actively growing in the field.

Recent studies with legumes have shown that oxygen plays a critical role in regulating root nodule metabolism and nitrogenase activity in legumes. The bacteria in the root nodules require large amounts of oxygen for respiration, yet oxygen is a potent irreversible inhibitor of the nitrogenase enzyme. Hence oxygen in the bacteria-infected cells must be maintained at a very low level. The nodule does this by regulating its permeability to $O_2$ diffusion from the soil environment into the bacteria-infected cells. The $O_2$ concentration is maintained at such a low level that it limits the supply of respiratory energy available for nitrogenase activity. Thus there is, under a wide range of environmental and physiological conditions, a strong correlation between infected cell oxygen concentration and nitrogenase activity. Nodule respiration and nodule permeability are also correlated with nitrogenase activity under many environmental and physiological conditions.

The oxygen concentration in the infected cells is too low to be measured by oxygen electrodes or by mass spectrometry, so the rapid measurement of oxygen concentration cannot be effected directly. However, the infected cells of legume nodules contain a high concentration of a red colored, myoglobin-like compound called leghemoglobin, which reversibly binds oxygen and acts to facilitate the diffusion of oxygen to the bacteria. When oxygen binds to leghemoglobin, it causes a change in the leghemoglobin absorption spectrum, and this change can be used as the basis for the spectrophotometric determination of fractional oxygenation of leghemoglobin. From the measurement of fractional leghemoglobin oxygenation, and a knowledge of the rate constants for leghemoglobin oxygenation and deoxygenation, an estimate of the free $O_2$ concentration in the infected cells can be calculated. Many non-leguminous $N_2$ fixing plants are also known to contain hemoglobins, and it should be possible to use the methodology described herein to measure the oxygen concentration in these nodules.

Hemoglobin oxygen saturation has been studied in mammalian systems for many years and there are several instruments, known as oximeters, available to measure non-invasively the proportion of hemoglobin oxygen saturation in blood. One such system is described in some detail in IEEE Trans. Biomed. Eng. 35: 185-197 (1988). However, these oximeters, which will be discussed in more detail hereinafter, are sensitive to ambient light, not designed for use with small nodules and therefore they are not suitable for agricultural field use.

OBJECT OF THE INVENTION

It is an object of the present invention to provide a simple method for determining oxygen concentration in legume nodules, nodule respiration rate and nodule permeability to $O_2$ diffusion and from one or more of these measurements estimate nitrogenase activity and biological nitrogen fixation in nitrogen fixing nodules.

It is another object of the present invention to provide an apparatus for measuring the oxygen concentration, respiration rate and $O_2$ permeability in nitrogen fixing legume nodules.

BRIEF STATEMENT OF INVENTION

By one aspect of this invention there is provided a non-invasive method for measuring infected cell oxygen concentration in a nodule of a nitrogen fixing plant comprising:

(a) directing modulated light of at least one wavelength to said nodule;

(b) detecting light passing through said nodule;

(c) measuring the said detected light while the said nodule is exposed to at least one selected gaseous atmosphere;

(d) measuring the fractional oxygenation of nodule hemoglobin from measurements of said detected light selected from the light detected at different wavelengths, and the light detected when the nodules are exposed to different gaseous atmospheres, and combinations thereof; and (e) calculating the said infected cell oxygen concentration within said nodule as a function of said fractional hemoglobin oxygenation.

By another aspect of this invention there is provided an apparatus for non-invasive measurement, in vivo, of the infected cell oxygen concentration in the nodule of a nitrogen fixing plant comprising:

(a) a source of modulated light having a peak output of at least one selected wavelength;

(b) means to direct said modulated light to a selected bacterially infected root nodule of said plant;

(c) means to detect light passing through said nodule thereof; and (d) means to measure said detected light while said nodule is exposed to at least one selected gaseous atmosphere.

DETAILED DESCRIPTION OF PREFERRED EMBODIMENTS

Figure 1:
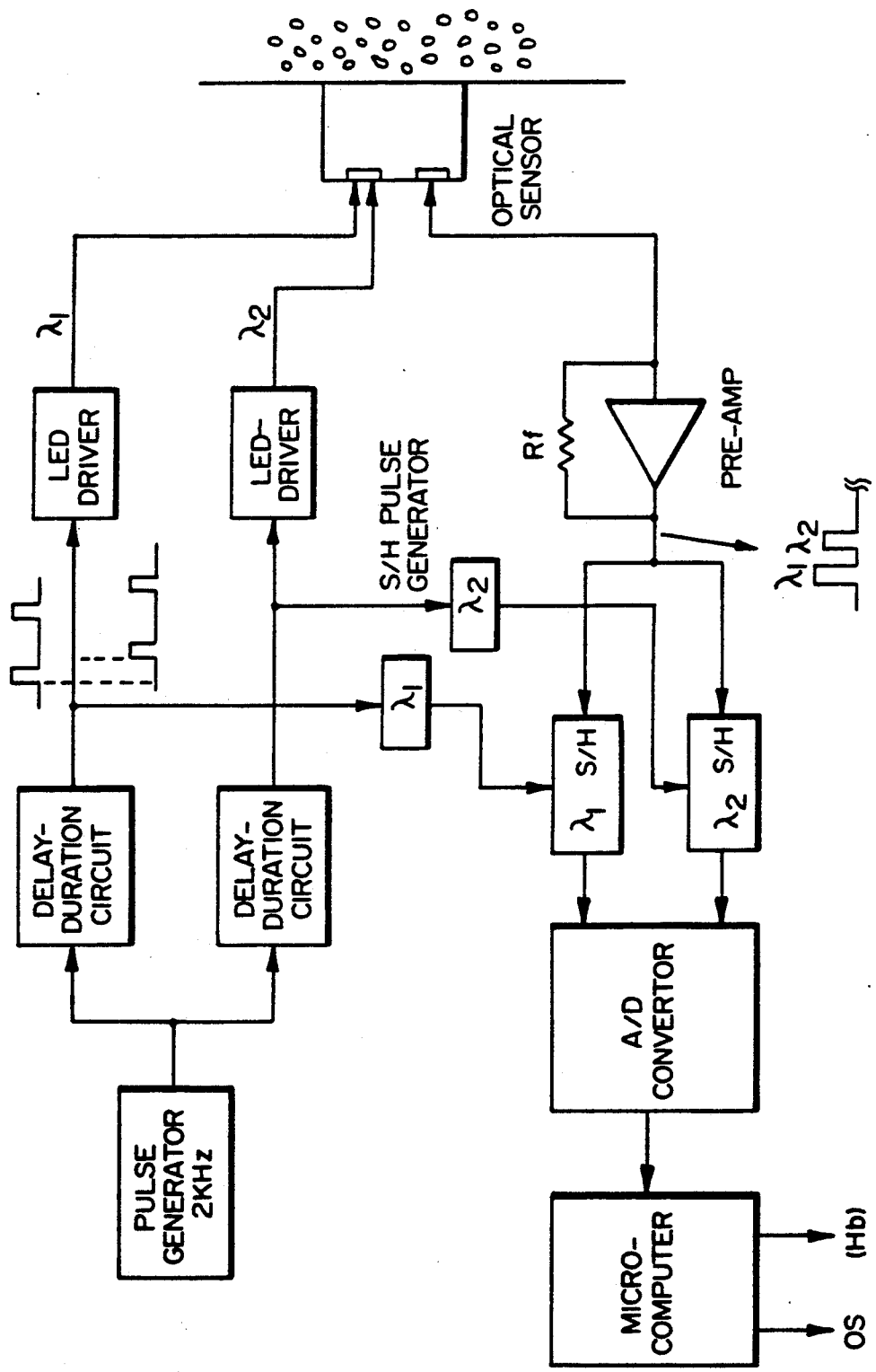
FIG. 1 is a block diagram of an oximeter according to the prior art.

In the oximeter system for determining hemoglobin and oxygen saturation in mammalian blood, illustrated in FIG. 1 an optical sensor, approximately 8 mm in diameter is provided with two light sources providing light at wavelengths of 665 and 795 nm with a photodetector optically separated therefrom. The sensor is placed directly on the flat skin surface and natural light is excluded by the opaque material of the sensor case and the skin. Exclusion of natural light from the vicinity of the optical sensor is necessary because the amplifier for the signal from the photo detector is not designed to discriminate the signal from any background signals. It will be appreciated that while it is a simple matter to select a mammalian skin area of sufficient size to cooperate with the sensor to exclude extraneous light, such is not the case when dealing with root nodules which are often only 1-8 mm in diameter and do not provide a sufficiently large relatively flat surface. To measure $O_2$ concentration in a root nodule there is a requirement for (a) a source of modulated light of a selected wavelength (b) a detection system to remove interference from outside light sources and (c) a small optical fiber positioned to maximize the capture of a proportion of the light passing through the central infected zone of the nodule.

A Single Channel Nodule Oximeter for Measurement of $O_i$

Figure 2:
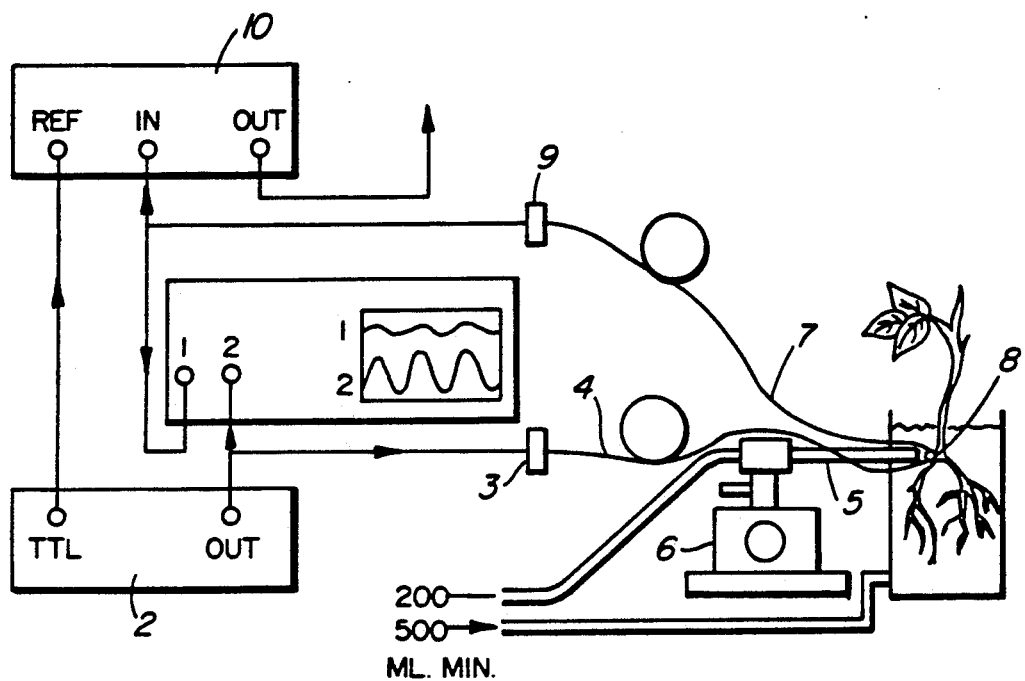
FIG. 2 is a block diagram of one embodiment of an apparatus according to the present invention.

One preferred embodiment of the apparatus is shown schematically in FIG. 2. A function generator 2 (Model 3011, BK Precision, Chicago Ill.), supplies a 1 kHz sine or square wave voltage to a light emitting diode 3, (LED, Model 0-0663, General Fiber Optics, Cedar Grove, N.J.), connected in series with a current-limiting 330 ohm resistor. The voltage fluctuations (+1.7 v to +10 v) are selected so that the intensity of the LED varies sinusoidally, or in a square wave between the maximum and minimum voltages, 1000 times per second. The power output from the function generator 2 is monitored using an oscilloscope 11 (Model 2120A, BK Precision, Chicago, Ill.). The LED emits light with a peak output at 660 nm, a wavelength at which large differences are seen in the oxygenated and deoxygenated spectra of leghemoglobin. The LED is coupled to one end of a 1 meter long optical fiber 4 (1 mm OD, plastic core) using a SMA connector (General Fiber Optic, Cedar Grove N.J.). The other end of the fiber is cleaned and polished and attached to a hollow brass probe 5 (as seen more clearly in FIG. 3) held by a micromanipulator 6. The probe is used to optimize the position of the input fiber 4 and the output optical fiber 7 such that the output fiber touches the surface of the nodule at right angles to the surface. The input fiber is positioned near, but not necessarily touching the nodule 8 under study. Light from the output cable 7 impinges on a photodiode 9 (Model SD 444-41-11-261, Silicon Detector Corp., Camarillo Calif.) the signal from which enters the input of a lock-in amplifier 10 (Model 3921, Ithaco, Ithaca, N.Y.). The reference signal for the amplifier is provided by the TTL output of the function generator 2 which is in phase with the sine wave or square wave voltage provided to the LED 3. The analog output signal from the lock-in amplifier 10 may be directed to a chart recorder or other voltage recording device (not shown). The lock-in amplifier measures only the signal from the photodiode which is in phase with the 1 KHz reference signal from the function generator 2. The amplifier thus eliminates any effect of non-modulated light entering the output optical fiber, greatly increasing the signal to noise ratio, and allowing all measurements of fractional leghemoglobin oxygenation to be made in room or natural light. The amount of 660 nm light reflected by, or transmitted through, the nodule is dependent on the absorbance of this light by leghemoglobin and, therefore, on the oxygenation state of the leghemoglobin in the infected cells.

For laboratory studies, legumes may be grown in pots provided with slits through which the probe 5 may be inserted, whereas in the field it would merely be necessary to loosen the soil around the roots and position the probe against an exposed nodule. In either case the aim is to measure the infected cell oxygen concentration ($O_i$) in the nodule and hence determine the biological activity of nitrogenase from empirically-derived relationships such as that shown in FIG. 5. The apparatus may also be used to study the effect of various physiological or environmental factors on the $O_i$, nitrogenase activity $N_2$ fixation rate, permeability to $O_2$ and the $O_2$ uptake rate in nodules of in experimental plants. The present apparatus is readily adaptable for this purpose in laboratory studies.

The hollow brass probe 5 may be connected to a gas mixing/supply system (not shown) and any desired gas or mixture of gases (e.g. $N_2$, $O_2$, Ar) can be flushed through the probe at an appropriate rate (e.g. 200–1000 $mL.min^{-1}$) allowing rapid and precise control of the atmosphere surrounding the selected nodule. There are various approaches to determine the fractional oxygenation of leghemoglobin in control and experimental nodules. In one approach, a $N_2:O_2$ (80:20) gas mixture is passed through the pot at 500 $mL.min^{-1}$ and through the probe 5 at 200 $mL.min^{-1}$ and the amount of modulated light reflected by the nodule is measured as a voltage output from the lock-in amplifier. When a steady signal has been attained, the gas through the pot and probe is switched to pure $N_2$ and the fully deoxygenated signal from the nodule is measured. When this signal is stable, the gas through the pot and probe is switched to pure $O_2$ and the fully oxygenated signal from the nodule is measured. Since the differences between the voltage signals from the lock-in amplifier at 0% (v/v) and 100% $O_2$ is small (typically 100 mV) compared to the overall voltage signal at each $pO_2$ (usually 1 to 4V), an offset control on the lock-in amplifier is used so that these differences can be easily observed on the chart recorder. After measurement of the signal at 100% $O_2$, power to the LED is terminated and a "dark voltage" is measured across the chart recorder terminals using a multimeter. This dark voltage is summed to each of the chart recorder voltage measurements to give the true signal from the nodule at each $pO_2$. Each voltage signal is then converted to an absorbance value using the following equation:

$$\text{Absorbance} = \ln\left[\frac{I_o}{I_i}\right] \qquad \text{Eqn 1.}$$

where $I_i$ is the voltage signal measured at each $pO_2$ and $I_o$ is an estimate of the voltage signal which would be obtained if all the incident radiation were to be supplied to the photodetector. $I_o$ is not measured directly but is set at a constant value equal to about ten times the typical $I_i$ values obtained in the experiments. As long as $I_o >> I_i$ (known to be the case since a small proportion of the incident light is returned to the photodetector), the magnitude of $I_o$ does not have a significant effect on the calculation of $O_i$ as described below.

The fractional oxygenation of leghemoglobin (Y) is then calculated using the equation:

$$Y = \frac{A_0 - A_{20}}{A_0 - A_{100}} \qquad \text{Eqn 2.}$$

where $A_0$ and $A_{100}$ are the absorbance values of leghemoglobin in its fully deoxygenated and fully oxygenated state respectively, and $A_{20}$ is the absorbance of leghemoglobin at 20% $O_2$. $O_i$ is then estimated by the following equation:

$$O_i = \frac{Y(k1/k2)}{100 - Y} \qquad \text{Eqn 3.}$$

where k1 and k2 are the rate constants for leghemoglobin deoxygenation and oxygenation, respectively, and values of k1 and k2 range from 30-100 nm and are preferably from 37-48 nm.

Measurement Of $O_i$ And Nitrogenase Activity Under Various Conditions

To demonstrate the use of the laboratory nodule oximeter, five groups of plants were tested: control, stem-girdled, dark-treated, disturbed and $NO_3^-$-treated. In all plants, $H_2$ evolution rates in $N_2:O_2$ (80:20) (Apparent Nitrogenase Activity) and in $Ar:O_2$ (80:20) (Total Nitrogen Activities, TNA) were measured at the beginning of each experiment after which the following treatments were imposed: (a) In each control plant, $O_i$ was measured on a single nodule immediately after the measurements of $H_2$ evolution rates. (b) In each stem-girdled plant, a 1 cm wide ring of "bark" was removed from the stem after the measurement of TNA. This treatment has been shown to reduce phloem sap supply to the nodule and to inhibit nitrogenase activity without interrupting the flow of xylem water to the shoot. $H_2$ evolution in $N_2:O_2$ (80:20) was monitored after girdling and when it had declined to minimum rates (90 to 120 min) TNA and $O_i$ were measured. (c) The dark-treated plants were maintained in a growth cabinet in continuous darkness for 72 h after which $H_2$ evolution in $N_2:O_2$ (80:20), TNA and $O_i$ were measured. (d) The disturbed plants were uprooted and shaken vigorously prior to measurement of $O_i$ and measurement of $H_2$ evolution in air and $Ar:O_2$. (e) The $NO_3^-$-treated plants were irrigated twice daily for 2 days with a nutrient solution supplemented with 10 mM $KNO_3$. $H_2$ evolution in $N_2:O_2$ (80:20), TNA and $O_i$ were measured 48 h after the first $NO_3^-$ application.

In all plants, after $O_i$ was measured, the nodulated roots were excised, removed from the pot and washed free of silica sand. The nodules were then picked and dried at 85° C. for 72 h and weighed.

To achieve a stable reflectance signal from the nodule, it was necessary to position the output optical fiber such that the flat end was in direct contact with the nodule surface. The positioning of the input fiber delivering the modulated light signal was less critical. Good results were obtained when it was positioned from 1 to 1.5 mm from the nodule surface at an angle of 40° between it and the uptake cable. The probe shown in FIG. 3 was used successfully on nodules having diameters of 2 to 8 mm, with best results obtained with nodules of 3 to 6 mm.

In the control plants with the gas flow rates used in these experiments, a change in $pO_2$ from 20% to 0% resulted in a rapid decrease in reflectance (increase in absorbance) and a new stable value was achieved within 15 to 20 s. When the gas was returned immediately to 20% $O_2$, the reflectance signal returned to its initial level suggesting that the a brief anaerobic treatment did not alter $O_i$ by affecting nodule permeability to $O_2$ or the respiratory capacity of the nodule. Longer term exposure to 0% $O_2$ did not cause any further decline in the reflectance signal indicating that leghemoglobin had become fully deoxygenated after 15 s. On exposure to 100% $O_2$, the maximum stable reflectance signal from the nodule was obtained in approximately 15 s and, since this signal did not increase with longer term exposure to 100% $O_2$, it was assumed that Lb was fully oxygenated under these conditions. Consequently, once the probe was situated appropriately on the nodule, it was possible to obtain the data for estimating $O_i$ in approximately 1 min.

The voltages that corresponded with nodule reflectances at 20, 0 and 100% $O_2$ were converted to absorbance values and from these values estimates were made of leghemoglobin fractional oxygenation and $O_i$ using Equations 2 and 3. The average $O_i$ value for 12 control plants was $17.8 \pm 1.9$ (SE) nm $O_2$. In the same plants, TNA was $175 \pm 10$ umol.g$^{-1}$ dry weight.h$^{-1}$.

All of the plants which were stem-girdled, dark-treated, $NO_3^-$-inhibited or physically disturbed, displayed pretreatment values for TNA which where similar to those of the control plants (data not shown). However, following these treatments, TNA values were 41, 15, 55 and 41% respectively, of the mean activity in the control plants (FIG. 5).

Significant differences between control and treated nodules were also observed in the time course of changes in leghemoglobin oxygenation observed during the measurements of $O_i$. In general, when the treated plants were exposed to 0% $O_2$, the change in nodule reflectance was less pronounced, but the time to reach a new stable voltage was greater than that in the control plants (20 to 40 s). The increase in reflected light following nodule exposure from 0 to 100% was similar to that in the control plants, but as in the transfer from 20 to 0%, the time to achieve a stable voltage was longer than that observed in nodules from the control plants (more than 15 s) Using the differences in the relative oxygenation of leghemoglobin, it was estimated that values for $O_i$ in the stem-girdled, dark-treated, $NO_3^-$-inhibited nodules and disturbed nodules were only 36, 21, 40 and 69% of the mean $O_i$ value obtained from the control plants ($17.8 \pm 1.9$ nm) (FIG. 5).

Figure 5:
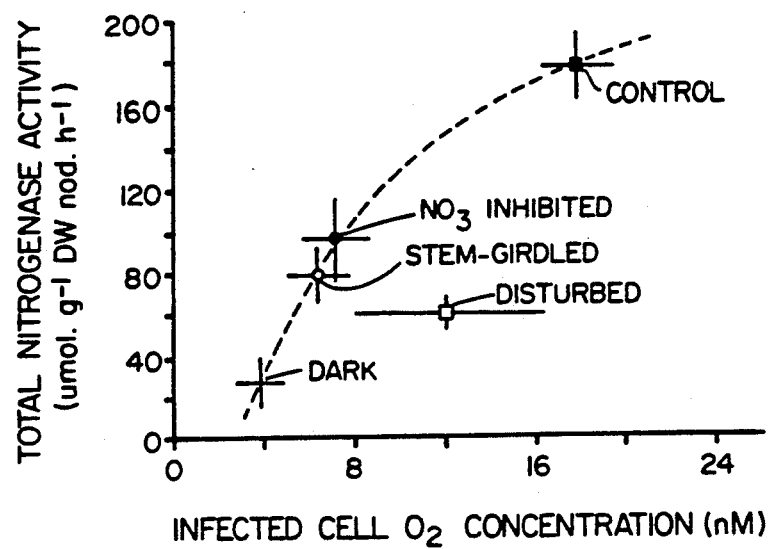
FIG. 5 illustrates the relationship between Total Nitrogenase Activity and Infected Cell Oxygen Concentrations in nodules exposed to various treatments.

In FIG. 5, the values for TNA (Total Nitrogenase Activity), were plotted against the estimates of $O_i$ for each of the treatments. The control treatment was highest and the dark treatment lowest for all parameters measured. In the plot of TNA versus $O_i$ (FIG. 5), a line connecting the dark-treated, stem-girdled, $NO_3^-$-inhibited and control plants formed an apparent hyperbolic relationship. Data for the disturbed nodules did not fit this pattern, but this was not seen to be a problem since this treatment is not likely to be relevant to most agricultural conditions.

Limitations Of The Single Channel Nodule Oximeter

Although the apparatus described above is well suited to laboratory experimentation, modification for field use would require: (a) improved stability, preferably to a point where the probe could be hand-held, (b) a modification of the method for calculating leghemoglobin oxygenation such that it will not be necessary to expose the nodules to the various gas phases which result in the conversion of leghemoglobin into the fully oxygenated and fully deoxygenated forms, (c) a reduction in the size and complexity of the instrumentation, and (d) an increase in its portability.

The use of dual or multiple wavelengths may satisfy the need for improved stability and the need for a simplified method for determining the proportion of leghemoglobin that is oxygenated. For example, if the nodule was illuminated with a second wavelength of light at which there was little change (or an opposite change) in light absorption with leghemoglobin oxygenation, the difference in absorption values at the two wavelengths should reduce or eliminate the effects of drift and greatly improve the stability of the signal with time. In addition, the ratio of light absorbance at the two wavelengths may provide a value which is directly proportional to leghemoglobin oxygenation among nodules; at least among those nodules belonging to plants of the same species. In the latter case, it may be necessary to compare the ratio of light absorption in air with that in an atmosphere lacking oxygen since the change in the absorption ratios between the fully deoxygenated and fully oxygenated form of Lb may be a constant.

A Dual Channel Nodule Oximeter

Figure 3:
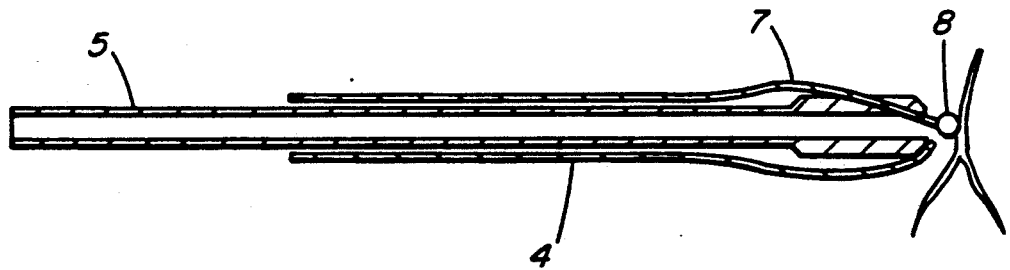
FIG. 3 is a cross sectional enlarged view of the probe used in the embodiment of FIG. 2.
Figure 4:
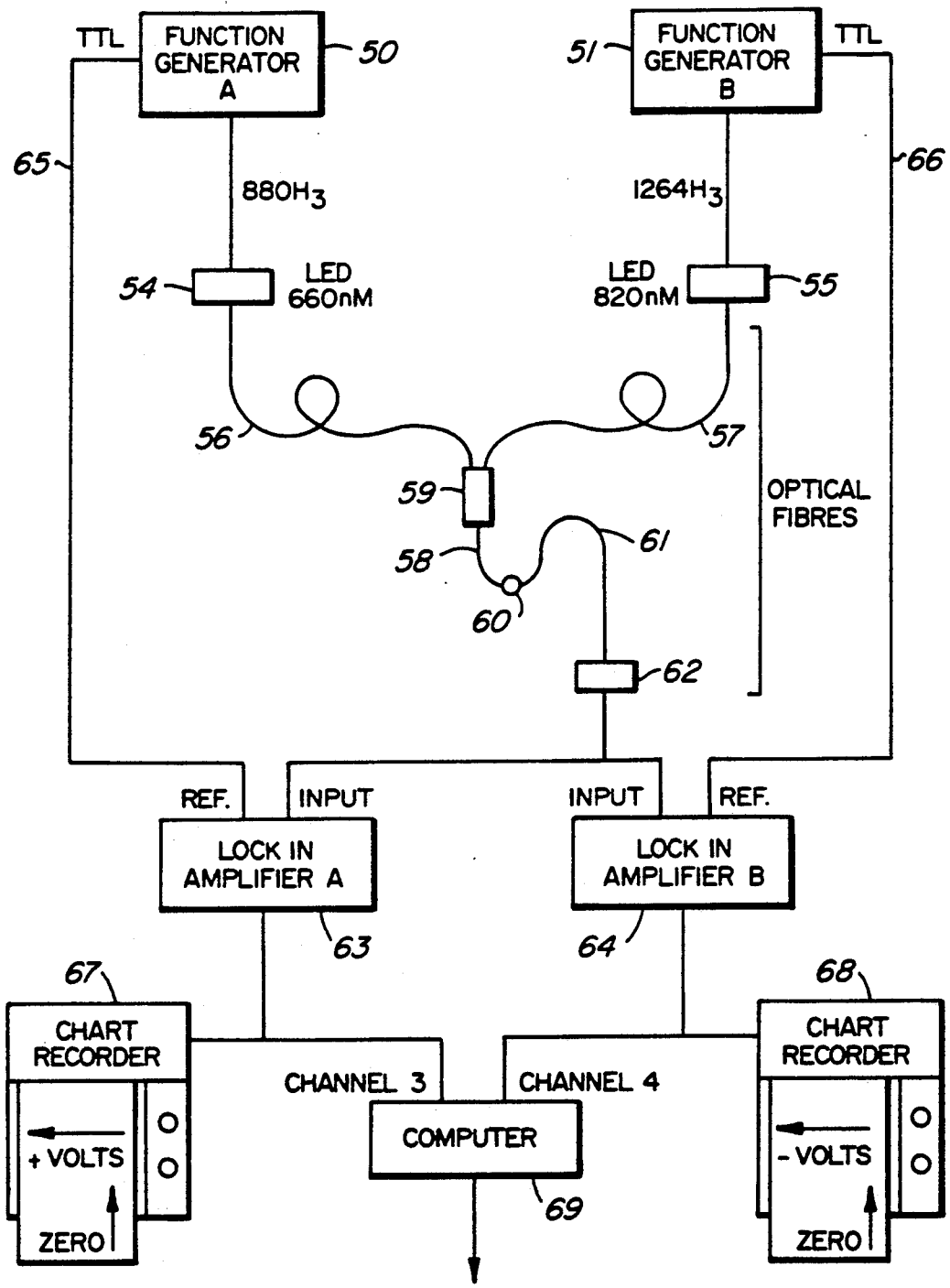
FIG. 4 is a block diagram of an alternative embodiment of the present invention incorporating two wavelengths of light.

In an alternative embodiment of the nodule oximeter, a dual wavelength version of the instrument has been shown to greatly improve its stability. This alternative design (FIG. 4) incorporates two light emitting diodes 54,55 providing peak outputs at 660 and 820 nm, respectively. The LEDs are powered by two function generators 50,51 set to provide square or sine-wave voltage fluctuations at different frequencies (660 nm at 880 Hz and 820 nm at 1264 Hz). The light from the two LEDs are coupled into two, 400 um optical fibers 56,57 which are in turn coupled to a single, 1 mm optical fiber 58 in a 3-way coupler 59 (General Fiber Optic, special order). The 1 mm optical fiber directs the light to the nodule 60 as in the previous system (FIG. 3). The output optical fiber 61 directs detected light to a photodetector 62, and the output of the photodetector 62 is supplied, in parallel, to two lock-in amplifiers 63,64. Each lock-in amplifier receives a reference signal 65,66 from one of the TTL outputs of the two function generators 50,51. The output voltages from the lock-in amplifiers 63,64 are provided to two recording devices (e.g. chart recorders 67,68 or to a dual channel analog to digital converter in a computer 69). The voltage values collected at the same time are subsequently subtracted from one another to provide a voltage signal which is less sensitive than the single detection system described previously to small movements in the position of the probe on the nodule. In an alternative design (not shown), the two output voltages from the lock-in amplifiers could be supplied to an operational amplifier which provides an output voltage equivalent to the difference between the two voltages.

Figure 6:
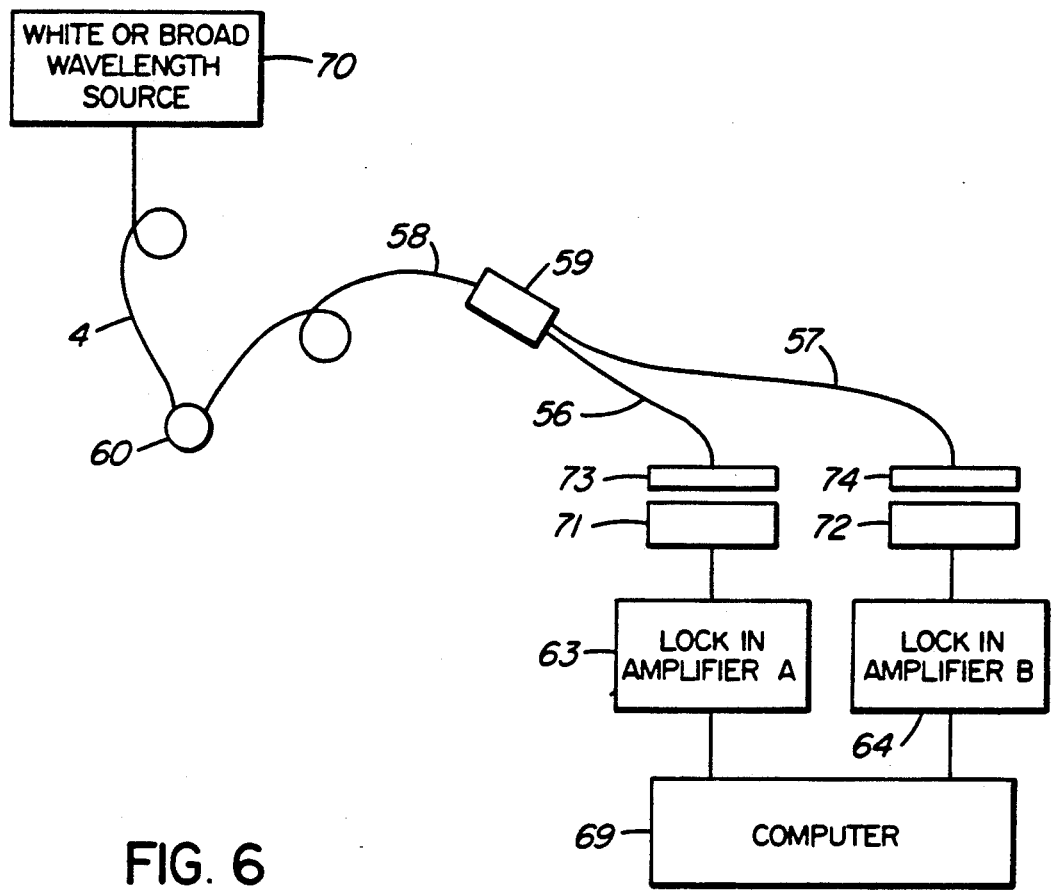
FIG. 6 is a block diagram of an alternative embodiment of the present invention incorporating broad wavelength or white light.

As noted above, the light supplied to the nodule is generally a single wavelength (e.g. 660 nm) or two wavelengths (e.g. 660 and 820 nm). These narrow band wavelengths can be supplied from various sources including LEDs, lasers or laser diodes, and may or may not be coupled to an optical fiber. Dual wavelengths from two sources would normally be coupled into a single optical fiber for delivery to the nodule. The present invention does, however, also envisage using a white light, or broad band wavelength light covering two regions of the leghemoglobin absorption spectrum (FIGS. 6 & 7); one where absorption changes with oxygenation and deoxygenation are large and one where the changes are either small or in the opposite direction.

The light as derived above is normally modulated as appropriate. Single and broad band wavelengths can be modulated at a single frequency as either a sine wave or square wave or any other wave form. Dual or multiple wavelength light sources can be modulated at different frequencies as sine, square or other wave form. Dual or multiple wavelengths can be modulated at the same frequency by offsetting in time such that no two light sources are on at the same time.

Figure 7:
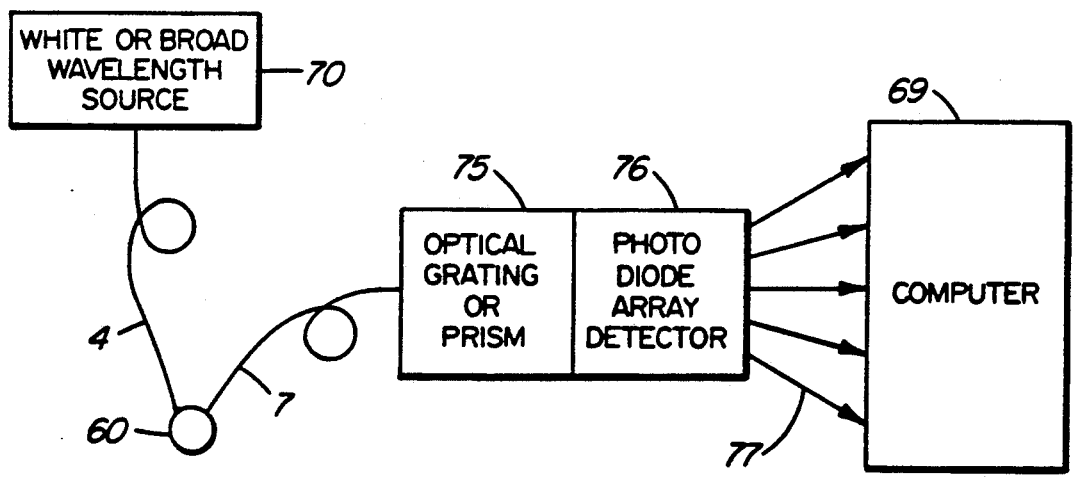
FIG. 7 is a block diagram of a further embodiment of the present invention incorporating broad wavelength or white light and a photodiode array detector.

Light detection and analysis can be achieved in various ways, including, but not exclusively, with the one or more lock-in amplifiers described in detail above or with other devices which will measure separately only the light signal in phase with each modulated light supply. For white light or broad band wavelength light 70 (FIGS. 6 & 7), one or more photodetectors 71,72 can be used with appropriate filters 73,74 (FIG. 6), optical gratings or a prism 75 (FIG. 7) to deliver selected wavelengths of light to the photodetectors. For example, multiple wavelengths of light could be detected by a photodiode array 76 (FIG. 7). The light signal from the photodetectors 77 may be analyzed, as before, by one or more lock in amplifiers 63,64 or other devices 69 which will measure, separately, only the light signal in phase with each modulated wavelength of interest.

A Computer Controlled Dual Channel Nodule Oximeter

An alternative apparatus for non-invasively measuring leghemoglobin oxygenation, which overcomes the need for much of the expensive and cumbersome electronic components described above, has also been developed, thus making a portable and inexpensive unit possible. Two units are described hereinafter, one (FIG. 8) is a laboratory based unit with excellent control over gas composition, and the other (FIG. 9) is a portable unit housed within a metal box 95 of approximately $48 \times 16 \times 16$ cm. The principle of operation for both instruments is similar to that described with reference to FIG. 4, but they have incorporated an instrumentation microcomputer 80 (SPCL-0004-X22, New Micros, Dallas Tex.) to replace most of the bulky and expensive electronics. As in the instrument described in FIG. 4, a second wavelength was used to correct for optical changes unrelated to leghemoglobin oxygenation. The red and infrared radiations were generated by light-emitting diodes 81,82 (LEDs; Motorola MFOE76 and MFOE71) coupled to a 1.0 mm O.D. fiber optic tree 83 (Aster Corp., Milford, Mass.). A small fraction of the radiation passing through the nodule was returned through a second optical fiber 84 to a photodetector 85 (OP5986, TRW, Carrollton Tex.). Output from the photodetector was amplified and low-pass filtered (circuitry not shown), then digitized by an A/D converter 86 and recorded by the instrumentation microcomputer 80. The microcomputer 80 also controlled the LEDs 81,82 through digital switches. Readings of photodetector output with the nodule illuminated successively by the red LED, the infrared LED, or ambient light only, were made at intervals of approximately 4 ms. The average reading for each mode of illumination was recorded every 0.5 s.

In the laboratory instrument (FIG. 8) the nodule atmosphere was controlled by the computer through three mass flow controllers 87,88,89 which determined the flow rate and therefore the composition of $O_2$, $N_2$ and Ar in the gas stream. One digital-to-analog channel (DAC, FIG. 8) of the computer was used to control each mass flow controller. The gas stream was humidified by passing through wet glass wool in humidifier 90. The portable instrument, (FIG. 9) differed from the laboratory version in the following ways:

(a) The gaseous environment of the nodule was controlled by the activation of solenoid valves 91,92 rather than by mass flow controllers. Therefore, there was no computer control over the flow rate of the gases. Since only two pressurized gases, $N_2$ 93 and $O_2$ 94, were supplied to the instrument, the instrument was only able to provide a pure $N_2$ (Solenoid valve 91 on) or a pure $O_2$ (Solenoid valve 92 on) atmosphere for the nodule. With both solenoid valves off, the nodule would be exposed to normal air.

(b) With the exception of the compressed gas cylinders 93,94, the optical fibers and gas line 5 leading to the nodule, all components of the instrument were contained in a metal box 95 measuring approximately 48×16×16 cm. (c) A DC-DC power supply 96 was incorporated to provide all necessary voltages from either a 12 volt battery 97 or an external 12 volt supply 98.

(d) Modifications to the circuit 99 and to the software (not shown) allowed the microcomputer to provide an offset voltage to the photodetector and active filter circuit 85. This allowed for increased sensitivity of the instrument to small changes in nodule transmittance.

(e) A speech synthesizer 100 and associated speaker 101 has been incorporated in the instrument and is currently under development. This component should allow the user to obtain information on the instrument output while concentrating on the placement of the optical fibers rather than watching a digital readout.

(f) All optical fibers and tubing supplied to or from the instrument are detachable. Brass bulkhead fittings 102 (Swagelok type) are used for all tubing connections, and a dual fiber optic bulkhead 103 is used for the optical fibers.

(g) A computer communications port 104 of the RS 232 type is also incorporated to transfer programs and data to and from the computer.

Figure 8:
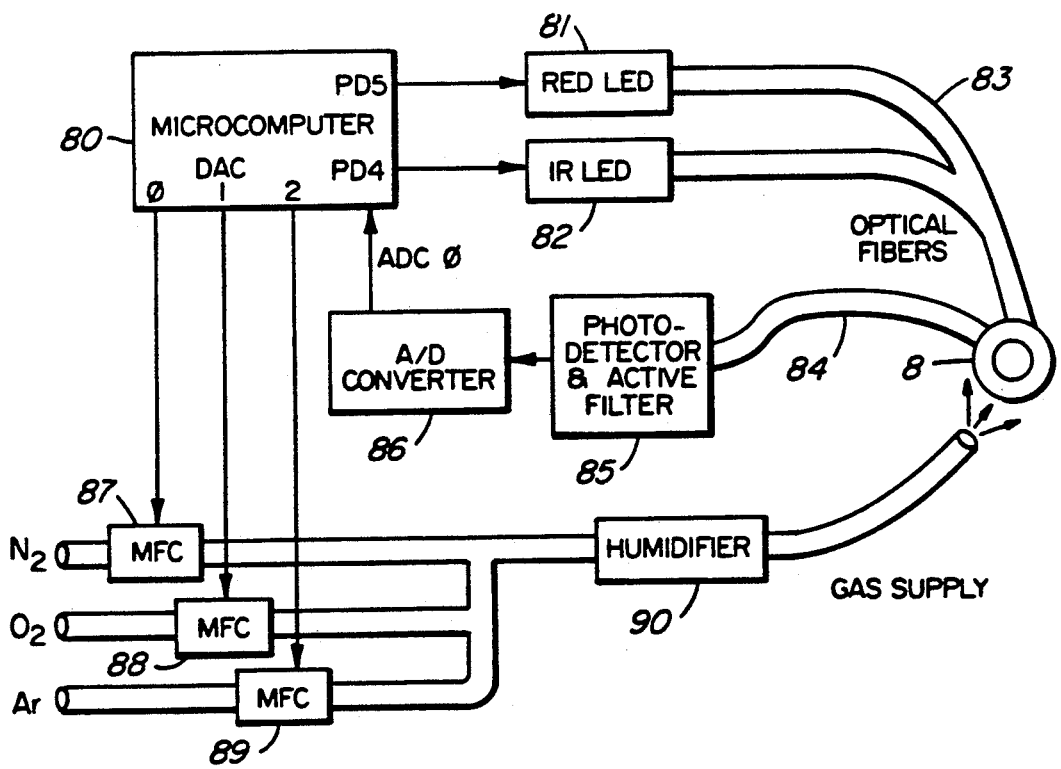
FIG. 8 is a block diagram of a further alternative embodiment of the present invention incorporating two wavelengths of light and computer control.
Figure 9:
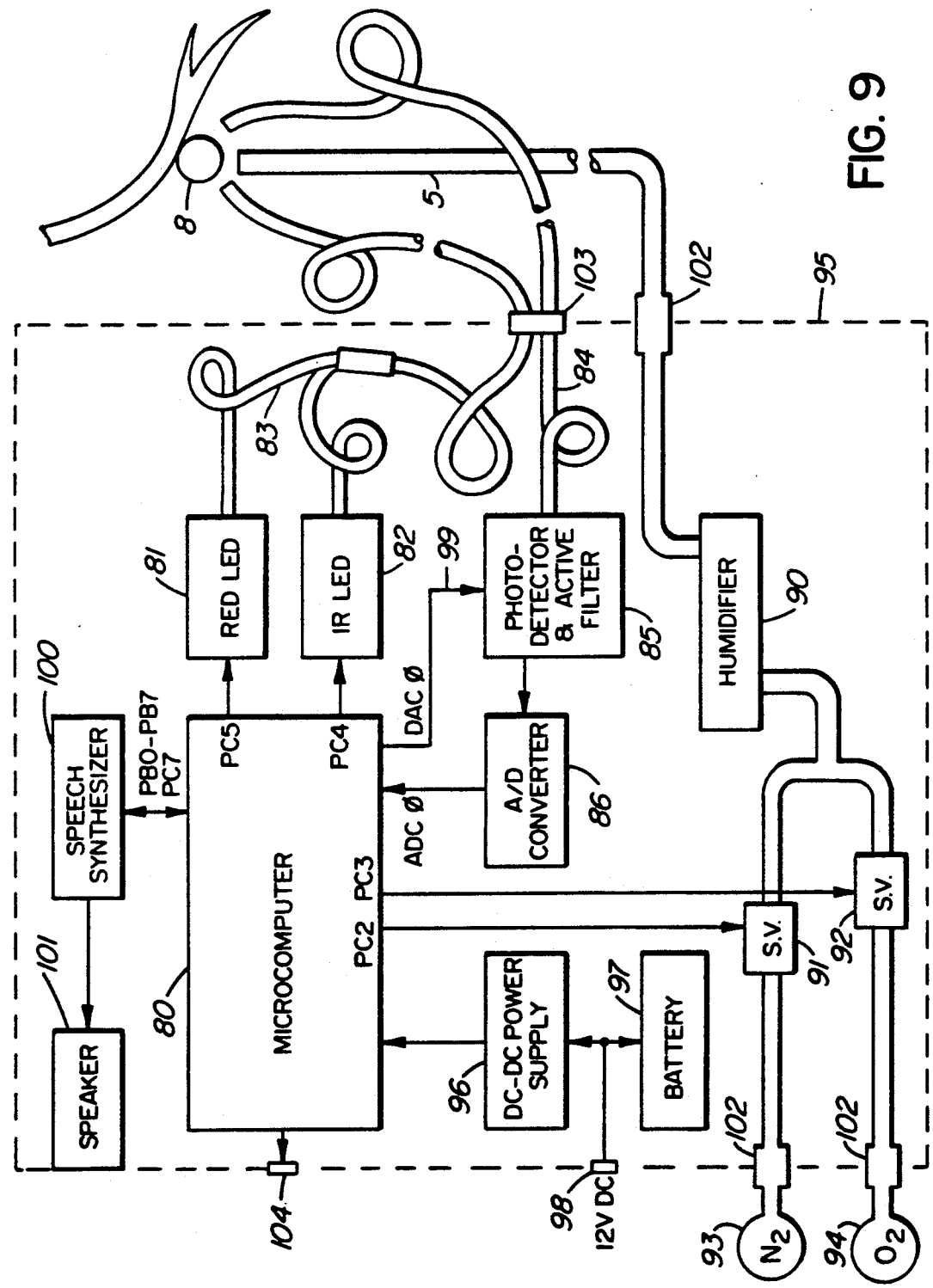
FIG. 9 is a block diagram of a further embodiment of the present invention, incorporating portability, two wavelengths of light and computer control.

In both of the instruments shown in FIGS. 8 & 9, fractional oxygenation of leghemoglobin (Y) and $O_i$ were calculated from the ratio of red:infrared transmittance, after subtracting ambient light. This ratio was used because of the assumption that transmittance at each wavelength could be approximated by a two-component version of the Beer-Lambert Law:

$$I_{660} = I_0 \cdot e^{-[f(t)+g(Y)]} \qquad \text{Eqn 4}$$

$$I_{820} = I_0 \cdot e^{-[f(t)+k]} \qquad \text{Eqn 5}$$

where $I_{660}$ and $I_{820}$ are the intensities of transmitted light at the two wavelengths, $I_0$ is the incident intensity for both wavelengths, t is time, and k is a constant which reflects possible differences (independent of Lb oxygenation) in absorbance with wavelength. The functions f(t) and g(Y) represent the assumptions that both wavelengths may be affected by some optical changes with time (e.g., slight movements of the probe or surface drying of the nodule), whereas only red light is affected by changes in Lb oxygenation. The ratio of red:infrared should eliminate the time dependence.

$$\frac{I_{660}}{I_{820}} = e^{-[g(Y)-k]} \qquad \text{Eqn 6}$$

Although use of the red:infrared ratio improved stability, successive readings at Y=0 still varied slightly over time for most nodules. Therefore, a linear correction for drift was also included.

$$Y = \frac{\ln(R_t) - \ln(R_0)}{\ln(R_{100}) - \ln(R_0)} \qquad \text{Eqn 7}$$

$$O_i = \frac{Y \cdot k_1/k_2}{1 - Y} \qquad \text{Eqn 8}$$

where $R_t$, $R_0$, and $R_{100}$ are the red:infrared ratios at any time, or the steady-state values obtained under 100% $N_2$ or 100% $O_2$, respectively (see below), and $k_1/k_2$ (ratio of reaction coefficients for Lb) was assumed to be to 37–48 nM. Steady-state values under $N_2$ and $O_2$ were assumed to correspond to full deoxygenation and full oxygenation of Lb, respectively.

In the standard assay for $O_i$ measurements using the dual wavelength instruments (FIGS. 8 & 9), the nodule was exposed first to 100% $N_2$, then to 100% $O_2$, and finally to 20% $N_2$. Each gas exposure was maintained until Y reached a steady state. Between standard assays, the nodule was exposed to 20% (v/v) $O_2$ in $N_2$, (except as noted). The gas flow rate was always 1.0 L min$^{-1}$ unless a measurement of $O_i$ at any other external $O_2$ concentration was required. The ratio of 660 nm/820 nm light transmittance was more stable with time than the voltage output of the single channel instrument, and $O_i$ could be readily calculated from Eqn 8.

A software program for use with the microcomputer provided the signals which were required to activate the Red and IR LED's >380 times per second and to provide a dark (both LED's off) signal >190 times each second. Coordinated with each event, the signal from the photodetector was read and stored. Approximately every 0.5–1.0 sec, the average dark signal was subtracted from the average Red & IR signal and the ratio of the Red:IR voltages for that time interval were stored in the computer memory. When the results from a typical run were converted into units of Y and plotted against time, results such as those shown in FIG. 10A were obtained.

Figure 10A:
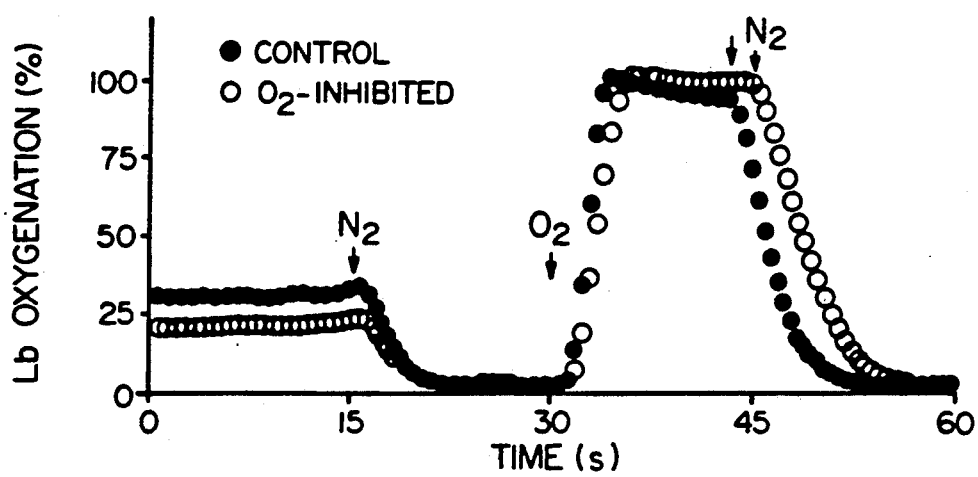
FIG. 10A, 10B & 10C are examples of a typical instrument output (A) from a computer-controlled oximeter such as those in FIG. 8 or 9, and the calculated relationship between nodule respiration and infected cell oxygen concentration (B) and nodule permeability to $O_2$ diffusion and infected cell oxygen concentration (C).

In this Figure, two treatments are shown, both using plants of Birdsfoot Trefoil. The 'Control' treatment was performed on plants under normal growth conditions, while the '$O_2$-inhibited' treatment involved exposing nodulated roots to 100% $O_2$ for 15 minutes. This treatment is thought to result in the destruction of nitrogenase activity and cause a decrease in both nodule respiration and nodule permeability to $O_2$ diffusion. The results in FIG. 10A show that the $O_2$-inhibited nodules had a lower Y, and therefore a lower $O_i$, than nodules of control plants.

The computer incorporated into the dual wavelength instrument also controls the mass flow controllers 87,88,89 (FIG. 8) or solenoid valves 91,92 (FIG. 9). In some versions of the software for these instruments, the computer monitors the photodetector output when the nodule is in the presence of $O_2$ and when the nodule hemoglobin becomes close to saturation, it automatically switches the atmosphere to one of $N_2$. This ensures that nitrogenase activity is not destroyed by exposure to excessive levels of $O_2$ gas.

Measurement Of Nodule Respiration And Oxygen Permeability

If it is assumed that a change in Y results from an imbalance between inward diffusion of $O_2$ and $O_2$ consumption in the nodule interior, infected-zone respiration ($O_2$ consumption) rate and nodule $O_2$ permeability may be calculated from the rate of change of Y following a change in the $O_2$ concentration around the nodule. Quantitatively, $$\frac{dLbO_2}{dt} = P \cdot A \cdot (O_e - [O_i/\alpha]) - \frac{V_{max} \cdot O_i}{K_m + O_i} \qquad \text{Eqn 9}$$

where $dLbO_2/dt$ is the rate of change in oxygenated leghemoglobin (mol m$^{-3}$s$^{-1}$), P is the nodule permeability (m/s), A is the surface area of the nodule diffusion barrier (m$^2$), $O_e$ is the gas-phase $O_2$ concentration external to the diffusion barrier (mol m$^{-3}$), $\alpha$ is the $O_2$ solubility in cytoplasm (assumed to be 0.03 mole in aqueous phase/mole in gas phase), $V_{max}$ is the maximum $O_2$ consumption rate in the nodule interior (mol m$^{-3}$s$^{-1}$), and $K_m$ is the value of $O_i$ for which $O_2$ consumption rate equals one-half of $V_{max}$. The first term on the right hand side of the equation represents inward $O_2$ diffusion (Fick's Law in one dimension), whereas the second term represents $O_2$ consumption in the nodule, assuming that the dependence of respiration rate on $O_i$ can be described by the Michaelis-Menten equation. Use of the solubility coefficient, $\alpha$, assumes $O_2$ equilibrium between the cytoplasm of infected cells and the intercellular air spaces. Although this assumption would not be strictly true under changing conditions, the difference $O_e - (O_i/\alpha)$ is quite insensitive to the value of $\alpha$, because $O_i$ is approximately zero. All calculations were implemented using MathCAD (MathSoft, Cambridge, Mass.).

The surface area of the diffusion barrier was calculated from the radius of the infected zone, measured with an ocular micrometer, based on the assumption that the infected zone was spherical. This is a reasonable approximation for the determinate nodules of birdsfoot trefoil. The concentration of oxygenated Lb was calculated from Y by assuming a total Lb concentration in the infected zone of 0.68 mol m$^{-3}$.

As Y decreased under 100% $N_2$, the rate of this decrease was used to calculate the respiration rate. Outward diffusion of $O_2$ into the external 100% $N_2$ atmosphere was assumed to be zero, because the gradient driving outward diffusion ($O_i$—zero) was negligible relative to that which drives inward diffusion under air ($O_e - O_i$). The $K_m$ and $V_{max}$ for $O_2$ consumption were calculated from the relationship between respiration rate and $O_i$, using the nonlinear curve-fitting capabilities of MathCAD. Oxygen permeability was then calculated from the rate of increase of Y under 100% $O_2$, using Equation 6, after correcting for respiration using the previously calculated $K_m$ and $V_{max}$.

Figure 10B:
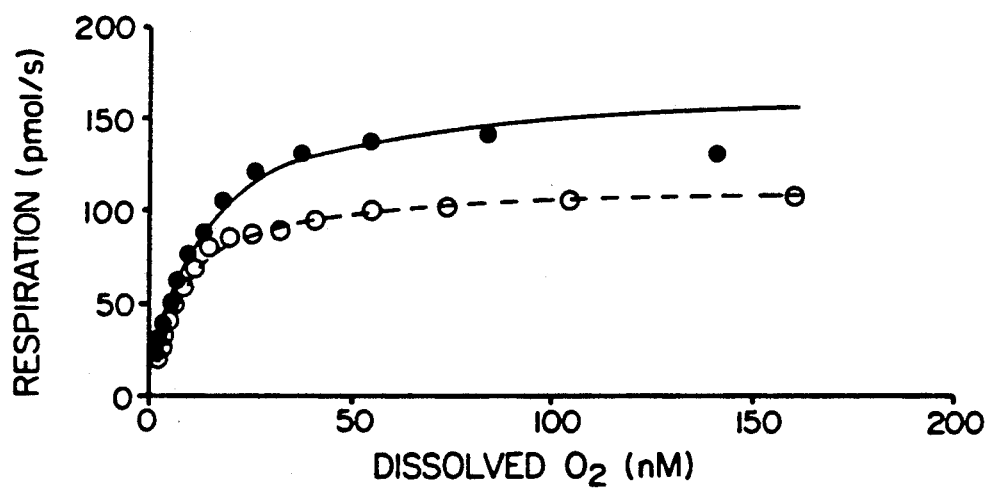
Figure 10C:
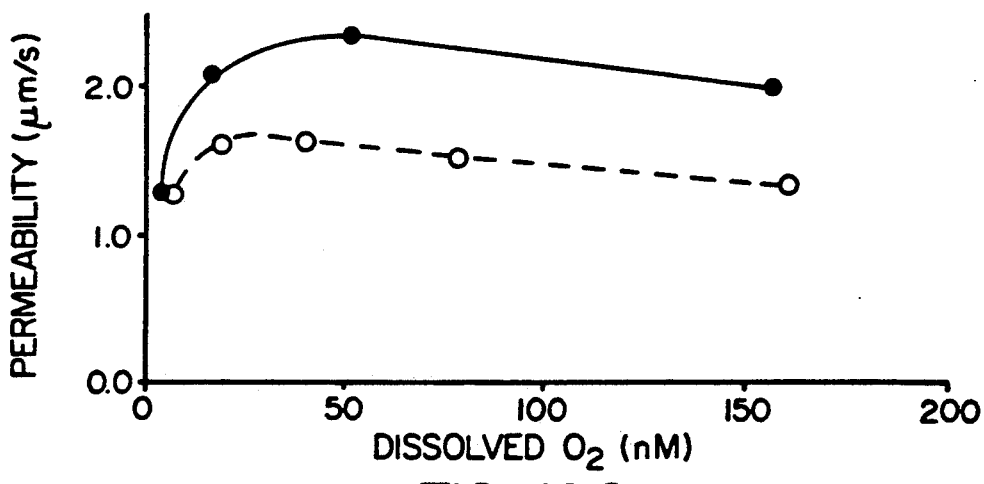

Calculations of nodule respiration rates and $O_2$ permeabilities have been carried out using the data of FIG. 10A and are shown in FIG. 10B and 10C, respectively. The results show that $O_2$-inhibited nodules have a lower respiration rate and a lower permeability to $O_2$ diffusion than do nodules from Control plants.

Advantages of the Computer Controlled Oximeters.

There are a number of advantages to the use of a single board computer rather than function generators 2,50,51 and lock-in amplifiers 10,63,64 to control the modulated LED's and analyze the photodetector signal. These include:

(a) a significantly lower cost, weight and power consumption, thereby making portability a realistic possibility;

(b) the ability to collect the data in a digital form thereby making it easy to carry out subsequent calculations of parameters such as nodule respiration of $O_2$ permeability.

We claim:

1. A non-invasive method for measuring infected cell oxygen concentration, in a nodule of a nitrogen-fixing plant comprising:

(a) directing modulated light of at least one selected wavelength to said nodule;

(b) detecting light passing through said nodule;

(c) measuring the said detected light while the said nodule is exposed to at least one selected gaseous atmosphere;

(d) measuring the fractional oxygenation of nodule hemoglobin from measurements of said detected light selected from the light detected at different wavelengths, and the light detected when the nodules were exposed to different gaseous atmospheres, and combinations thereof; and (e) calculating the oxygen concentration within said nodule as a function of said fractional hemoglobin oxygenation.

2. A method as claimed in claim 1 including the step of calculating oxygen respiration rate by measuring the rate of decrease in said oxygen concentration with time following exposure of said nodule to a low external oxygen concentration.

3. A method as claimed in claim 2 including the step of calculating nodule oxygen permeability by measuring the rate of increase in said oxygen concentration with time following exposure of said nodule to a high external oxygen concentration and correcting said rate of increase for the measurement of said oxygen respiration rate for each said infected cell oxygen concentration.

4. A method as claimed in claim 1 wherein modulated light of two selected wavelengths is directed at said nodule.

5. A method as claimed in claim 4 wherein one said wavelength is selected from wavelengths at which there is a significant change in light absorption by said nodule hemoglobin between an oxygenated and a deoxygenated form.

6. A method as claimed in claim 5 wherein the second said wavelength is selected from wavelengths at which there is a change in light absorption by said nodule hemoglobin between the oxygenated and deoxygenated forms selected from an insignificant change and a change in the opposite direction.

7. A method as claimed in claim 5 wherein said selected wavelengths are between about 630 and 680 nm.

8. A method as claimed in claim 6 wherein said selected wavelengths are between 790 and 850 nm.

9. A method as claimed in claim 7 wherein one said selected wavelength is about 660 nm.

10. A method as claimed in claim 8 wherein the second said selected wavelength is about 820 nm.

11. A method as claimed in claim 1 wherein said selected wavelength light is transmitted through an optical fiber having its output end closely adjacent to the said nodule.

12. A method as claimed in claim 11 wherein said detected light is transmitted to a photodiode detector by an optical fiber adjacent to said nodule.

13. A method as claimed in claim 12 wherein an output signal from said detector is processed in a lock-in amplifier.

14. A method as claimed in claim 12 wherein an output signal from said detector is processed in a computer.

15. A method as claimed in claim 1 including providing an atmosphere selected from the group consisting of oxygen, nitrogen, argon and mixtures thereof around said nodule.

16. A method as claimed in claim 1 including the step of estimating nitrogenase activity of said nodule as a function of said fractional oxygenation of nodule hemoglobin.

17. A method as claimed in claim 1 wherein modulated light is from a source selected from the group consisting of white light and broad-band wavelength light.

18. A method as claimed in claim 17 wherein said broad band wavelength light comprises light covering (a) a region of the nodule hemoglobin absorption spectrum in which large absorption changes occur with oxygenation and deoxygenation and (b) a region of the nodule hemoglobin absorption spectrum in which insignificant or reverse changes occur with oxygenation and deoxygenation.

19. An apparatus for non-invasive measurement, in vivo, of infected cell oxygen concentration in nitrogen fixing plants comprising:
   (a) a source of modulated light having a peak output of at least one selected wavelength;
   (b) means to direct said modulated light to a selected bacterially infected root nodule of said plant;
   (c) means to detect light passing through said nodule, thereof; and
   (d) means to measure said detected light while said nodule is exposed to at least one selected gaseous atmosphere.

20. An apparatus as claimed in claim 19 including (e) means to record rate of change in said detected light while said nodule is exposed to said selected gaseous atmosphere.

21. An apparatus as claimed in claim 19 wherein said means to direct said modulated light is an optical fiber.

22. An apparatus as claimed in claim 19 wherein said means to detect said modulated light includes an optical fiber.

23. An apparatus as claimed in claim 19 wherein said means to detect said modulated light includes photodetecting means.

24. An apparatus as claimed in claim 19 wherein said means to measure said detected light comprises a phase sensitive device.

25. An apparatus as claimed in claim 24 wherein said phase sensitive device comprises a lock-in amplifier adapted to receive an output signal from said means to detect and a reference signal in phase with the modulated light directed to said module.

26. An apparatus as claimed in claim 25 including means to receive and record an output signal from said lock-in amplifier.

27. An apparatus as claimed in claim 19 including means to provide an atmosphere selected from the group consisting of oxygen, nitrogen, argon and mixtures thereof around said selected nodule.

28. An apparatus as claimed in claim 27 wherein said means to provide an atmosphere includes a hollow gas probe.

29. An apparatus as claimed in claim 28 wherein said means to direct light and said means to detect light are operatively mounted on said gas probe.

30. An apparatus as claimed in claim 29 including means to manipulate and position said probe relative to said nodule.

31. An apparatus as claimed in claim 19 including means to generate modulated light of two selected wavelengths.

32. An apparatus as claimed in claim 31 wherein said selected wavelengths are 660 nm and 820 nm respectively.

33. An apparatus as claimed in claim 19 wherein said source of modulated light is selected from the group consisting of (a) a single wavelength source; (b) dual wavelength sources coupled to a single optical fiber for delivery to the nodule; and (c) a white or broad wavelength light source covering at least two regions of the nodule hemoglobin absorption spectrum.

34. An apparatus as claimed in claim 33 wherein said modulated light is selected from the group consisting of (a) a single or broad wavelength modulated at a single frequency; (b) dual or multiple wavelengths modulated at different frequencies; and (c) dual or multiple wavelengths modulated at the same frequency, but offset in time so that no two light sources are active at the same time.

35. An apparatus as claimed in claim 34 wherein said light is modulated in a form selected from the group consisting of sine wave and square wave.

36. An apparatus as claimed in claim 21 wherein said means to measure said detected light is selected from the group consisting of at least one lock in amplifier and a device for separately measuring only a light signal in phase with each modulated light source.

37. An apparatus as claimed in claim 33 wherein said modulated light is detected by at least one photodetector.

38. An apparatus as claimed in claim 33 wherein said modulated light is selected from the group consisting of white light and broad band wavelengths and including filter means to select specific wavelengths for photodetection.

39. An apparatus as claimed in claim 33 wherein said modulated light is selected from the group consisting of white light and broad band light wavelengths and including means selected from an optical grating and a prism for delivering said modulated light to a photodiode array, thereby permitting measurement of selected wavelengths.

40. An apparatus as claimed in claim 24 wherein said phase sensitive device comprises microcomputer means adapted to receive an output signal from said means to detect.

41. An apparatus as claimed in claim 40 including means to receive and record an output signal from said microcomputer means.

42. An apparatus as claimed in claim 40 including speech synthesizer means controlled by said microcomputer means.

43. An apparatus as claimed in claim 40 including container means so as to provide a portable device.

* * * * *